United States Patent [19]

Hasselbach et al.

[11] Patent Number: 6,150,563
[45] Date of Patent: Nov. 21, 2000

[54] ALIPHATIC ALKANALS WITH IMPROVED STORAGE STABILITY AND METHOD OF IMPROVING THE STORAGE STABILITY

[75] Inventors: Hans Joachim Hasselbach; Klaus Huthmacher, both of Gelnhausen; Katja Kelm, Kahl; Horst Weigel, Rodenbach, all of Germany

[73] Assignee: Degussa-Huls AG, Frankfurt am Main, Germany

[21] Appl. No.: 09/134,562

[22] Filed: Aug. 14, 1998

[30] Foreign Application Priority Data

Aug. 14, 1997 [DE] Germany .............................. 197 35 332

[51] Int. Cl.⁷ ..................................................... C07C 47/00
[52] U.S. Cl. ............................................. 568/422; 568/421
[58] Field of Search ...................................... 568/422, 421

[56] References Cited

U.S. PATENT DOCUMENTS 4,289,912  9/1981  Harris ...................................... 568/422
4,546,205  10/1985  Sandler ................................... 568/421

FOREIGN PATENT DOCUMENTS

WO93/13059  7/1993  WIPO .

OTHER PUBLICATIONS

Derwent Publications Ltd., London, GB; Class D23 AN 92–431227, XP002087426 (Jan. 15, 1992).

*Primary Examiner*—Sreeni Padmanabhan
*Attorney, Agent, or Firm*—Pillsbury Madison & Sutro LLP

[57] ABSTRACT

Aliphatic alkanals with a water content of greater than 300 ppm which are stable in storage, and a method of improving the storage stability of these aliphatic alkanals, especially of substituted, sulfur-containing alkanals. The formation of oligomers, polymers and condensation products from elimination reactions and oxidation and the subsequent reactions of the products formed results in undesired impurities that are largely prevented by the addition of an organic acid that forms metal complexes and, optionally, alkanolamines or trialkanolamines.

10 Claims, No Drawings

ALIPHATIC ALKANALS WITH IMPROVED STORAGE STABILITY AND METHOD OF IMPROVING THE STORAGE STABILITY

BACKGROUND OF THE INVENTION

1. Field of the Invention

The present invention relates to storage stability of aliphatic alkanals with a water content of greater than 300 ppm and to a method of improving the storage stability of these aliphatic alkanals, especially of substituted, sulfur-containing alkanals. It is known that members of this family of compounds are very reactive and that changes occur during storage.

A large number of undesired impurities arise from the formation of oligomers, polymers and condensation products, as well as from elimination reactions and oxidation and the subsequent reactions of the products formed.

Retardation of formation of undesired higher-molecular weight resultant products by means of suitable additives in a low dosage is described.

2. Description of Related Art

It is known that the formation of byproducts during the storage of alkanals can be influenced by alkaline or basic conditions. In an acidic environment the formation of oligomers, polymers and, especially, cyclic trimers (trioxans) are favored. In an alkaline environment the condensation of aldols is favored. DE-OS 2,095,267 discloses the use of triethanolamine or N,N-dimethylethanolamine for stabilizing aldehydes before cyclic trimerization, polymerization and autocondensation occur. Japanese patents JP 72 321 963 and JP 49 116017 disclose using alkylated anilines for stablizing aldehydes. U.S. Pat. No. 4,546,205 concerns use of a mixture of a pyridine and a phenol component as an aldehyde stablizing agent.

The stabilizers cited produce a basic environment and reduce the rate of the acid catalyzed reactions. The stabilizers may be toxic and are used in high concentrations, preferably up to 0.2%. Purification by distillation is often not possible because of the boiling points and the product properties.

PCT WO 93/13059 describes the stabilization of sulfur-substituted alkanals with a mixture of an amine component together with an oxygen-binding component such as phenols or acidic or unsaturated antioxidants such as ascorbic acid or betacarotene. However, this method is only effective if the water content of the alkanal is below 300 ppm, preferably below 100 ppm.

Such a water content can only be achieved at considerable expense under production conditions. A nitrogen atmosphere is customarily used in order to avoid autooxidation. None of the methods described for the stabilization of alkanals, however, meets the requirement that the stabilization takes place with non-toxic substances at low concentrations and that a water content of up to 2% can be tolerated.

SUMMARY OF THE INVENTION

An object of the present invention is to provide aliphatic alkanals that are stable in storage, and that have the general formula

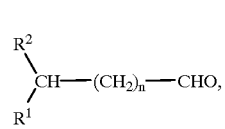

in which
$R^1$, $R^2$ are the same or different and are: hydrogen or $C_{1-3}$ alkyl or one of $R^1$ and $R^2$ is a $C_{1-2}$ alkylthio group, and n is an integer from 0 to 4, having a water content of greater than 300 ppm and containing a saturated organic acid that forms metal complexes. These acids do not need to display the antioxidizing action required in the state of the art. Methylmercaptopropanal (MMP) is a preferred alkanal to be stablized using this method.

Applicants have found that, in addition to suppression of the aldol reaction by the addition of the acidic compounds, the formation of cyclic trimers favored in the acid is also considerably delayed. The water content of up to 2% by weight customary in industrial alkanals does not adversely affect the stabilization, especially where the alkanal is methylmercaptopropanal.

The preferred acidic compounds are compounds which are capable, on account of their structure, of complexing metals. Examples of preferred acidic compounds are: hydroxydicarboxylic acids such as e.g. citric acid, tartaric acid or malic acid, and especially aminotrismethylene phosphonic acid (ATMP).

In the case of tartaric acid there is no difference in the action between chiral tartaric acid and the racemate; however, the chiral form is preferred on account of its greater solubility and especially preferred is L-tartaric acid, on account of its availability.

The acids can be added in solid form or as a solution e.g. in water or a lower alcohol. Use in solution form has the advantage of providing rapid homogenization. The choice of the type of addition is made to prevent the formation of a second phase. The form of the addition is without significance for the action as stabilizer.

The stabilizing action continues up to a temperature of at least 50° to 100° C., preferably up to 60° C.

The specimens are preferably placed in a nitrogen atmosphere. An effective amount of acid is approximately 25 to 1000 mg acid/kg alkanal, preferably 40 to 600 mg acid/kg alkanal.

The activity of the acids, especially tartaric acid, can be improved by the addition of an alkanolamine, ($C_1$–$C_3$ alkanol), preferably trialkanolamines, and results in the use of less acid stabilizer. The amount of alkanolamines, preferably of trialkanolamines, and more preferably triethanolamine, in this mixture is in a range of 20 to 80%, preferably 40 to 70% by weight relative to the acid, the acid preferably being tartaric acid.

Of this mixture, especially a mixture of tartaric acid and triethanolamine, an amount of 50 to 150 mg/kg alkanal is sufficient to improve the long-term storage stability. The addition of the mixture also advantageously takes place in this instance as a concentrated aqueous solution of the two components. The formation of condensation products and oligomerization products is also clearly retarded by the addition of aminotrismethylene phosphonic acid (ATMP). A dosage concentration of 5 to 20 mg/kg alkanal is sufficient. Higher dosages (e.g., 100 mg/kg) result in, for example, yellowing of methylmercaptopropanal.

DETAILED DESCRIPTION OF THE INVENTION

The following examples are intended to illustrate the invention in a detailed, non-limiting manner. The rate of undesired reactions is low at a low temperature. In order to illustrate the influence of the stabilizers, temperatures above a normal storage temperature were selected.

In order to evaluate the stabilizer action untreated control specimens and specimens with stabilizer additive from the same batch were stored under isothermal conditions and analyzed after several weeks.

The sum of the oligomers, polymers and polycondensation products was determined from the distillation residue under standardized conditions. The determination of the cyclic trimers took place by 1H-NMR spectroscopy in the original specimen.

Example 1

500 g methylmercaptopropanal (MMP) with a water content of 2.0% by weight is mixed in a glass flask with 500 mg of a 50% aqueous solution of L-tartaric acid and stored together with a control specimen from the same production batch in a thermostatically controlled chamber at 30° C. After 50 and 70 days, 100 g is distilled from each of the specimen and the control specimen under standard conditions of 15 mbar, and up to 140° C. and the amount of residue is determined.

Residue in % by weight

| Storage time | Control specimen | Specimen |
|---|---|---|
| 50 days | 11.0 | 3.4 |
| 70 days | 28.3 | 5.0 |

Example 2

500 g methylmercaptopropanal (MMP) with a water content of 1.8% by weight is agitated in a glass container with 250 mg L-tartaric acid until the solid is dissolved. The air is displaced by introducing argon. A control specimen from the same batch is treated in the same manner. The storage takes place at 50° C. A determination of the residue takes place after 20, 50 and 70 days.

Residue in % by weight

| Storage time | Control specimen | Specimen |
|---|---|---|
| 20 days | 9.3 | 2.0 |
| 50 days | 22.3 | 3.1 |
| 70 days | 33.6 | 4.3 |

The control specimen contains 7.0% trimeric MMP after 20 days; in the stabilized specimen the trimer content is still below 1% after 70 days.

Example 3

An aqueous solution of 40% by weight L-tartaric acid and 20% by weight triethanolamine is used as stabilizer. 500 g methylmercaptopropanal (MMP) is mixed with 63 mg of the stabilizer solution and stored together with a control specimen from the same batch in a thermostat at 30° C.

Residue in % by weight

| Storage time | Control specimen | Specimen |
|---|---|---|
| 20 days | 1.5 | 0.9 |
| 50 days | 16.0 | 1.6 |

Example 4

Example 3 is repeated with an alkanal from the same batch; however, the specimens are stored at 50° C.

Residue in % by weight

| Storage time | Control specimen | Specimen |
|---|---|---|
| 20 days | 2.5 | 1.7 |
| 50 days | 18.9 | 4.5 |

Example 5

Comparative example. 500 g methylmercaptopropanal (MMP) with a water content of 1.8% by weight is provided in a glass container with 450 mg triethanolamine and 50 mg ascorbic acid and the mixture agitated until a clear solution is produced. This specimen is stored together with a control specimen at 50° C. The distillation residue is determined after 20 and after 50 days.

Residue in % by weight

| Storage time | Control specimen | Specimen |
|---|---|---|
| 20 days | 2.5 | 8.9 |
| 50 days | 22.3 | 20.0 |

After 50 days the control specimen contains 16.4% trimer, the treated specimen <1% trimer.

Example 6

500 g methylmercaptopropanal (MMP) are mixed with 20 mg of a 50% aminotrismethylene phosphonic acid solution (ATMP) and this specimen is stored together with a control specimen from the same batch at 50° C.

Residue in % by weight

| Storage time | Control specimen | Specimen |
|---|---|---|
| 20 days | 3.8 | 3.1 |
| 50 days | 27.6 | 5.2 |

Example 7

500 mg of a 50% L-tartaric acid solution are dissolved in 500 g isobutyraldehyde (for synthesis, Merck Co., Darmstadt) and the specimen stored together with a control specimen from the same batch at 30° C.

Residue in % by weight

| Storage time | Control specimen | Specimen |
|---|---|---|
| 21 days | 1.2 | 1.0 |
| 94 days | 12.4 | 4.1 |

Example 8

Of 6 steel containers with 20 tons methylmercaptopropanal (MMP) each, containers 1 to 3 are each stabilized with 10 kg L-tartaric acid. All containers remain standing in the open and the content is analyzed after 38 days.

Distillation residue is measured in % by weight. At the start of the storage period, the residue is 0.53%.

Residue in % by weight

| Container | Residue | Increase |
|---|---|---|
| 1, stabilized | 1.25 | 0.72 |
| 2, stabilized | 1.02 | 0.49 |
| 3, stabilized | 1.17 | 0.64 |
| 4, non-stabilized | 1.91 | 1.38 |
| 5, non-stabilized | 2.31 | 1.73 |
| 6, non-stabilized | 1.79 | 1.26 |

An average increase of 0.62% is calculated therefrom for the stabilized item and 1.47% for the non-stabilized item.

What is claimed is:

1. A composition comprising:
   (i) an aliphatic alkanal of formula (I):

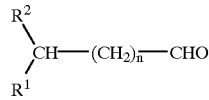

(I)

wherein $R^1$ and $R^2$ are the same or different and are selected from hydrogen or $C_{1-3}$ alkyl; or one of $R^1$ and $R^2$ is a $C_{1-2}$ alkylthio, and the other of $R^1$ and $R^2$ is selected from hydrogen or $C_{1-3}$ alkyl; and n is an integer from 0 to 4;
   (ii) water in an amount of greater than 300 ppm; and
   (iii) a saturated organic acid that is capable of forming metal complexes, wherein said saturated organic acid is tartaric acid in chiral or racemic form;

wherein said composition exhibits an improved storage stability.

2. The composition according to claim 1, comprising tartaric acid in an amount of 0.004 to 0.1% by weight relative to the amount of alkanal.

3. The composition according to claim 1, further comprising alkanolamine or trialkanolamine.

4. The composition according to claim 3, wherein said trialkanolamine comprises $C_1$ to $C_3$ trialkanolamine.

5. The composition according to claim 3, wherein said trialkanolamine is present in an amount of 20 to 80% by weight relative to the tartaric acid.

6. A method of improving the storage stability of an aliphatic alkanal of formula (I):

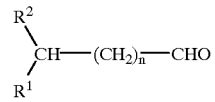

(I)

wherein $R^1$ and $R^2$ are the same or different and are selected from hydrogen or $C_{1-3}$ alkyl; or one of $R^1$ and $R^2$ is a $C_{1-2}$ alkylthio, and the other of $R^1$ and $R^2$ is selected from hydrogen or $C_{1-3}$ alkyl; and n is an integer from 0 to 4; comprising:

adding a saturated organic acid that is capable of forming metal complexes, wherein said saturated organic acid is tartaric acid in chiral or racemic form, and is optionally in the form of an aqueous or alcoholic solution, to the aliphatic alkanal having a water content of greater than 300 ppm.

7. The method according to claim 6, comprising adding tartaric acid in an amount of 0.04 to 0.1% by weight relative to the amount of alkanal.

8. The method according to claim 6, comprising:
   adding an alkanolamine or trialkanolamine.

9. The method according to claim 8, comprising adding trialkanolamine in an amount of 20 to 80% by weight relative to tartaric acid.

10. The method according to claim 8, comprising:
    adding 0.005 to 0.015% by weight of tartaric acid relative to the alkanal.

* * * * *